(12) United States Patent
Tanaka et al.

(10) Patent No.: US 9,039,826 B2
(45) Date of Patent: May 26, 2015

(54) CARDANOL-MODIFIED SILANE COUPLING AGENT, CARDANOL-MODIFIED FILLER, AND CELLULOSE RESIN COMPOSITION

(75) Inventors: Shukichi Tanaka, Tokyo (JP); Masatoshi Iji, Tokyo (JP)

(73) Assignee: NEC Corporation, Tokyo (JP)

(*) Notice: Subject to any disclaimer, the term of this patent is extended or adjusted under 35 U.S.C. 154(b) by 447 days.

(21) Appl. No.: 13/583,569

(22) PCT Filed: Dec. 3, 2010

(86) PCT No.: PCT/JP2010/071665
§ 371 (c)(1),
(2), (4) Date: Sep. 7, 2012

(87) PCT Pub. No.: WO2011/111272
PCT Pub. Date: Sep. 15, 2011

(65) Prior Publication Data
US 2013/0036940 A1  Feb. 14, 2013

(30) Foreign Application Priority Data

Mar. 11, 2010  (JP) .................. 2010-054419

(51) Int. Cl.
| C07F 7/18 | (2006.01) |
| C08L 1/02 | (2006.01) |
| C08K 5/54 | (2006.01) |
| C08K 5/5455 | (2006.01) |
| C08K 5/5435 | (2006.01) |
| C08K 9/06 | (2006.01) |

(52) U.S. Cl.
CPC .............. *C07F 7/1836* (2013.01); *C08K 5/5455* (2013.01); *C08K 5/5435* (2013.01); *C08K 9/06* (2013.01); *C07F 7/1812* (2013.01); *C08L 1/02* (2013.01); *C08K 5/54* (2013.01)

(58) Field of Classification Search
CPC ........ C07F 7/1836; C07F 7/1812; C08L 1/02; C08K 5/54; C08K 5/5455; C08K 9/06
See application file for complete search history.

(56) References Cited

U.S. PATENT DOCUMENTS

| 3,845,008 | A * | 10/1974 | Mitchell ........................ 523/157 |
| 5,504,123 | A | 4/1996 | Partan, III |
| 6,375,789 | B1 | 4/2002 | Katz et al. |
| 6,534,568 | B1 | 3/2003 | Katz et al. |
| 7,390,900 | B2 | 6/2008 | Seong et al. |
| 2005/0277774 | A1 | 12/2005 | Seong et al. |
| 2012/0202926 | A1 * | 8/2012 | Iji et al. ........................... 524/41 |
| 2013/0305959 | A1 * | 11/2013 | Moon et al. .................. 106/170.2 |
| 2013/0331518 | A1 * | 12/2013 | Immonen et al. ........... 525/54.21 |

FOREIGN PATENT DOCUMENTS

| CN | 1263541 A | 8/2000 |
| CN | 1771251 A | 5/2006 |
| CN | 101151217 A | 3/2008 |
| JP | H9-25395 A | 1/1997 |
| JP | 10-008035 A | 1/1998 |
| JP | 11-255801 A | 9/1999 |
| JP | 2001-032869 A | 2/2001 |
| JP | 2004-352939 A | 12/2004 |
| JP | 2006-219648 A | 8/2006 |
| JP | 2010-083943 A | 4/2010 |
| WO | WO 2008/137706 A1 | 11/2008 |

OTHER PUBLICATIONS

Chinese Office Action dated Apr. 28, 2014, with partial English translation.
George John et al., Polymer Bulletin, 22, p. 89-94(1989).
Joseph Kuruvilla et al., Polymer, 37, p. 5139-5149(1996).
D.T.Minh, et al., Chemical Abstracts, vol. 143, p. 995. abs No. 249057 (2005).
N.D.Chatge, et al., Chemical Abstracts, vol. 113, p. 42. abs No. 7403 (1990).
Kuruvilla Joseph, et al. "Effect of Chemical Treatment on the Tensile Properties of Short Sisal Fibre-Reinforced Polyethylene Composites" Polymer, vol. 37, No. 23, pp. 5139-5149 (1996).
Chemical Abstracts, vol. 143, p. 995 Abstract No. 249057 (2005).
Chemical Abstracts, vol. 113, p. 42 Abstract No. 7403 (1990).
Japanese Office Action dated Oct. 28, 2014 with an English translation thereof.

* cited by examiner

*Primary Examiner* — David M Brunsman
(74) *Attorney, Agent, or Firm* — McGinn IP Law Group, PLLC

(57) ABSTRACT

An exemplary embodiment provides a cardanol-modified silane coupling agent, which can improve strength and toughness by improving adhesion at an interface between a filler and a cellulose resin when being used as a surface-treatment agent, a resin additive, or the like; a cardanol-modified filler subjected to a surface treatment with the cardanol-modified silane coupling agent; and a cellulose resin composition having excellent toughness. More specifically, the exemplary embodiment provides a cardanol-modified silane coupling agent obtained by reacting cardanol or a derivative thereof with an epoxy silane coupling agent or an isocyanate silane coupling agent; a cardanol-modified filler obtained by subjecting a filler to a surface treatment with the cardanol-modified silane coupling agent; a cellulose resin composition comprising the cardanol-modified filler and a cellulose resin; and a cellulose resin composition comprising the cardanol-modified silane coupling agent, a filler and a cellulose resin.

20 Claims, No Drawings

US 9,039,826 B2

CARDANOL-MODIFIED SILANE COUPLING AGENT, CARDANOL-MODIFIED FILLER, AND CELLULOSE RESIN COMPOSITION

This application is a 371 filing of PCT/JP2010/071665, filed Dec. 3, 2010.

TECHNICAL FIELD

Exemplary embodiments according to the present invention relate to a cardanol-modified silane coupling agent, a cardanol-modified filler subjected to a surface treatment with the cardanol-modified silane coupling agent, and a cellulose resin composition having excellent toughness.

BACKGROUND ART

Bioplastics derived from plant have become more important, because they can contribute various measures to oil depletion and global-warming. Further, because of concerns about future food shortages, it has become necessary to develop new bioplastics using a plant material of inedible parts.

As bioplastics utilizing inedible parts, plastics have been already developed and become commercial, in which an acid such as acetic acid and nitric acid or a petroleum-based modifier such as alcohol, for example, butyl alcohol is chemically bonded to cellulose, a primary constituent of inedible parts, and further a plasticizer and the like are added as required. For instance, Patent Document 1 discloses a thermoplastic biodegradable graft polymer, in which ε-caprolactone is grafted to cellulose acetate having a hydroxyl group through ring-opening polymerization.

However, since cellulose-based bioplastics are insufficient in mechanical properties such as strength, rigidity, toughness and the like, as compared to conventional petroleum-based plastics, utilization of cellulose-based bioplastics to durable products such as electronic equipment and automobiles has not yet proceeded. To expand utilization of cellulose-based bioplastics to these products, it is required to improve mechanical properties thereof further.

As means for improving mechanical properties of such bioplastics, a method is effective, in which a particulate, plate-like or fibrous filler is added, and farther a silane coupling agent or the like is used, thereby improving adhesion at an interface between the filler and a resin. In application to durable products, epoxy-based or amino-based silane coupling agents are effectively used together with, primarily, inorganic fillers, and have been used for many years. Further, a method of adding a nano-sized filler to form a nanocomposite is also effective, because the nano-sized filler has a feature that can substantially reduce the addition amount thereof, as compared to a normal-sized filler.

Meanwhile, the development of materials utilizing inedible part constituents other than cellulose has also been carried out. For instance, cardanol derived from cashew nut shells has been used for various purposes because of its excellent functionality owing to its distinctive molecular structure, in addition to stable production thereof.

As an example of the use of cardanol, Patent Document 2 discloses a friction material for brakes, which is formed using a fiber substrate comprising an aramid pulp and a cellulose fiber, filler comprising calcium carbonate and cashew dust, and a binder comprising a phenolic resin. Further, Patent Document 3 discloses a friction material formed using a base material comprising an aramid fiber and a cellulose fiber, a filler comprising graphite and cashew dust, and an organic/inorganic composite binder, and describes that this frictional material is used for clutch facing of drivelines for automobiles and the like.

Non-Patent Document 1 describes that water resistance of paper can be improved by performing a grafting reaction in which a paper sheet is dipped in cardanol to bond the cardanol to cellulose composing this paper sheet. It is described that in this grafting reaction, a terminal double bond of cardanol is bonded to a hydroxyl group of cellulose in the presence of boron trifluoride diethylether ($BF_3$—$OEt_2$).

Non-Patent Document 2 describes that tensile strength of a polyethylene resin is improved by bonding an isocyanate compound obtained by reacting cardanol with tolylene diisocyanate to a surface of sisal fiber.

PRIOR ART DOCUMENTS

Patent Document

Patent Document 1: JP11-255801A
Patent Document 2: JP10-8035A
Patent Document 3: JP2001-32869A

Non-Patent Document

Non-Patent Document 1: George John et al., Polymer Bulletin, 22, p. 89-94 (1989)
Non-Patent Document 2: Joseph Kuruvilla et al., Polymer, 37, p. 5139-5149 (1996)

SUMMARY OF INVENTION

Technical Problem

When a filler subjected to a surface treatment with a conventional silane coupling agent is added to a cellulose bioplastic, the strength and rigidity are improved, but are still insufficient, and further causing a problem with a reduction in toughness. Furthermore, the isocyanate compound obtained by reacting cardanol with diisocyanate, which is described in Non-Patent Document 2, can be bonded to a surface of a cellulose-based filler such as sisal fiber but cannot be sufficiently bonded to a surface of an inorganic filler, which has higher rigidity and allows for fine dispersion, and the effect is also insufficient. Therefore, in order to apply bioplastics to durable products, particularly, to outer jackets etc. for electronic equipment, there is a need to further improve these properties.

An object of an exemplary embodiment according to the present invention is to provide a cardanol-modified silane coupling agent, which can improve strength and toughness by improving adhesion at an interface between a filler and a cellulose-based resin when being used as a surface-treatment agent, a resin additive, or the like; a cardanol-modified filler subjected to a surface treatment with the cardanol-modified silane coupling agent; and a cellulose resin composition being excellent in toughness.

Solution to Problem

The present inventors carried out extensive studies and examinations on the above-mentioned object and have found that when a cardanol-modified silane coupling agent (C) obtained by reacting cardanol or a derivative thereof (A) with an epoxy silane coupling agent or an isocyanate silane coupling agent (B) is used as a surface-treatment agent for filler or a resin additive, the cardanol-modified silane coupling agent (C) can improve strength by improving adhesion between a filler and a cellulose resin and can also improve toughness by an interaction of flexible straight-chain hydrocarbon parts of the cardanol or the derivative thereof.

That is, according to a first aspect of the present invention, a cardanol-modified silane coupling agent (C) obtained by reacting cardanol or a derivative thereof (A) with an epoxy silane coupling agent or an isocyanate silane coupling agent (B) is provided.

According to a second aspect of the present invention, a cardanol-modified filler (D), wherein a filler (D0) is subjected to a surface treatment with the cardanol-modified silane coupling agent (C), is provided.

According to a third aspect of the present invention, a cellulose resin composition comprising the cardanol-modified filler (D) and a cellulose resin (E0) is provided.

According to a fourth aspect of the present invention, a cellulose resin composition comprising the cardanol-modified silane coupling agent (C), a filler (D0), and a cellulose resin (E0) is provided.

Advantageous Effects of Invention

According to an exemplary embodiment of the present invention, it is possible to provide a cardanol-modified silane coupling agent, which can improve strength and toughness by improving adhesion between a filler and a cellulose resin when being used as a surface-treatment agent, a resin additive, or the like; a cardanol-modified filler subjected to a surface treatment with the cardanol-modified silane coupling agent; and a cellulose resin composition having excellent toughness.

MODES FOR CARRYING OUT THE INVENTION

1. Cardanol-Modified Silane Coupling Agent (C)

A cardanol-modified silane coupling agent (C) according to the exemplary embodiment is one obtained by reacting cardanol or a derivative thereof (A) (hereinafter also referred to as "constituent (A)") with an epoxy silane coupling agent or an isocyanate silane coupling agent (B) (hereinafter also referred to as "constituent (B)"). According to this reaction, the constituent (A) is bonded to the constituent (B), and it is possible to obtain a composition containing a compound which has an alkoxysilyl group being excellent in reactivity with a surface of a filler, together with a flexible and hydrophobic molecular structure of cardanol, being excellent in affinity with resins.

Cardanol is a constituent contained in cashew nut shells, and as represented by the below-described Formula (A1), it is an organic compound composed of a phenol moiety and a straight-chain hydrocarbon moiety. The straight-chain hydrocarbon moiety of cardanol come in four types, and cardanol is a mixture composed of the four constituents. As constituent (A), it is possible to use a cardanol constituent obtained by extracting a liquid from cashew nut shells and refining the liquid. Further, as constituent (A), it is also possible to use a hydrogenated cardanol in which an unsaturated bond in the straight-chain hydrocarbon moiety of cardanol is hydrogenated and converted into a saturated bond.

[Chemical Formula 1]

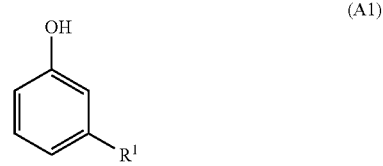

R$^1$: —(CH$_2$)$_{14}$CH$_3$
—(CH$_2$)$_7$CH=CH(CH$_2$)$_5$CH$_3$
—(CH$_2$)$_7$CH=CHCH$_2$CH=CH(CH$_2$)$_2$CH$_3$
—(CH$_2$)$_7$CH=CHCH$_2$CH=CHCH$_2$CH=CH$_2$

An epoxy silane coupling agent is a silane coupling agent containing one or more epoxy group(s) in one molecule. Examples of the epoxy silane coupling agent include γ-glycidyloxy propyl trimethoxy silane, γ-glycidyloxy propyl triethoxy silane, β-(3,4-epoxycyclohexyl) ethyl trimethoxy silane, γ-glycidyloxy propyl methyl diethoxy silane, and γ-glycidyloxy propyl methyl dimethoxy silane. Among these, a silane compound represented by the following Formula (B1) is preferred.

[Chemical Formula 2]

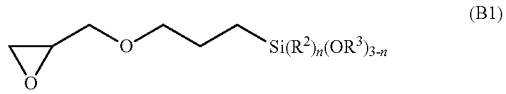

R$^2$ and R$^3$: alkyl group having carbon atoms of 1 to 4;
n = 0 or 1.

An isocyanate silane coupling agent is a silane coupling agent containing one or more isocyanate group(s) in one molecule. Examples of the isocyanate silane coupling agent include γ-isocyanatopropyl trimethoxy silane, γ-isocyanatopropyl triethoxy silane, γ-isocyanatopropyl methyl diethoxy silane, and γ-isocyanatopropyl methyl dimethoxy silane. Among these, a silane compound represented by the following Formula (B2) is preferred.

[Chemical Formula 3]

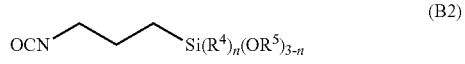

R$^4$ and R$^5$: alkyl group having carbon atoms of 1 to 4;
n = 0 or 1.

The epoxy silane coupling agent and the isocyanate silane coupling agent being constituent (B) may be used alone or in combination.

In a reaction between constituents (A) and (B), a phenolic hydroxyl group possessed by constituent (A) is bonded to an epoxy group in the epoxy silane coupling agent being (B) constituent or an isocyanate group in the isocyanate silane coupling agent being constituent (B). This reaction can be performed by adding constituent (B) in 0.9 to 1.5 equivalents and a catalyst to one equivalent of constituent (A) heated at 60° C. to 120° C., and as for the reaction time, for example, about 30 minutes to about 2 hours is adequate. By setting the reaction temperature to 60° C. or higher, constituent (A) is melted, and it becomes easier to make the reaction system homogeneous. By setting the reaction temperature to 120° C. or lower, constituent (B) becomes less volatilized, and a quantitative reaction easily proceeds. Further, by setting the addition amount of constituent (B) to 0.9 equivalents or more, the residue amount of unreacted constituent (A) decreases, making it possible to inhibit decreases in physical properties when being added to a resin. By setting the addition amount of constituent (B) to 1.5 equivalents or less, gelation caused by a reaction among excessive amounts of constituent (B) can be suppressed.

The catalyst can be catalysts or accelerating agents generally used for a reaction between an epoxy group and a phenolic hydroxyl group, or between an isocyanate group and a phenolic hydroxyl group. Examples of the catalysts used for the reaction between an epoxy group and a phenolic hydroxyl group include phosphorus compounds, tertiary amines, imidazoles, organometallic salts, Lewis acids, and amine complex salts. Among these, from the viewpoint of high catalytic ability and ease of handling, phosphorous compounds or imidazoles are preferred, and triphenylphosphine or 2-ethyl-4-methyl imidazole is more preferred. Examples of the catalysts used for the reaction between an isocyanate group and a phenolic hydroxyl group include tertiary amines such as triethyl amine, and benzyl methyl amine; and stannous organic acid ester compounds such as dibutyl tin dilaurate and tin octylate. Among these, from the viewpoint of high catalytic ability and ease of handling, the stannous organic acid ester compounds are preferred, and dibutyl tin dilaurate is more preferred.

The addition amount of the catalyst to constituent (A) is preferably approximately 0.01 mol % to 2 mol %. By setting the addition amount of the catalyst to 0.01 mol % or more, the reaction time can be shortened, and the production efficiency increases. By setting the addition amount of the catalyst to 2 mol % or less, gelation caused by a reaction among (B) constituents can be reduced. These catalysts may be added after being dissolved in a small amount of an organic solvent such as chloroform, hexane, toluene, and dioxane.

At the time of performing this reaction, a solvent is not particularly required, but an organic solvent such as chloroform, toluene, and dioxane may be used as a solvent. Note that since this reaction takes against water, this reaction is preferably performed under an atmosphere of a moisture-fee gas, such as dry nitrogen and argon, so that water is not mixed in the reaction system.

A cardanol-modified silane coupling agent (C) obtained by this reaction, for instance, in the case where cardanol is used as constituent (A), and a silane compound represented by Formula (B1) or (132) described above is used as constituent (B), is in a form of a mixture primarily containing a cardanol-modified alkoxysilane compound represented by the following Formula (C1) or (C2) and containing an intermolecular condensate and an intramolecular condensate of the cardanol-modified alkoxysilane compound. The compounds contained in the mixture can be isolated by refining through a known method such as a method of using a difference in solubility, and column chromatography. Note that these compounds are not necessarily isolated, and using the mixture in its natural state is simple and preferred.

[Chemical Formula 4]

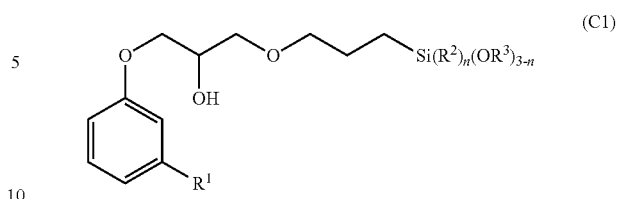

(C1)

$R^1$: ——$(CH_2)_{14}CH_3$
——$(CH_2)_7CH$═$CH(CH_2)_5CH_3$
——$(CH_2)_7CH$═$CHCH_2CH$═$CH(CH_2)_2CH_3$
——$(CH_2)_7CH$═$CHCH_2CH$═$CHCH_2CH$═$CH_2$ $R^2$ and $R^3$: alkyl group having carbon atoms of 1 to 4;
n = 0 or 1.

[Chemical Formula 5]

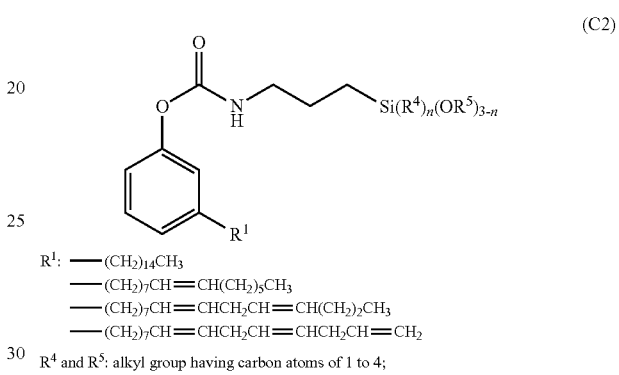

(C2)

$R^1$: ——$(CH_2)_{14}CH_3$
——$(CH_2)_7CH$═$CH(CH_2)_5CH_3$
——$(CH_2)_7CH$═$CHCH_2CH$═$CH(CH_2)_2CH_3$
——$(CH_2)_7CH$═$CHCH_2CH$═$CHCH_2CH$═$CH_2$ $R^4$ and $R^5$: alkyl group having carbon atoms of 1 to 4;
n = 0 or 1.

2. Cardanol-Modified Filler (D)

A cardanol-modified filler (D) according to the exemplary embodiment is one obtained by subjecting a filler (D0) to a surface treatment with the cardanol-modified silane coupling agent (C). By this surface treatment, the filler (D0) is made to be the cardanol-modified filler (D), in which a compound contained in the cardanol-modified silane coupling agent (C) is bonded to a surface of the filler (D0). In this way, by subjecting the filler (D0) to a surface treatment with the cardanol-modified silane coupling agent (C), the hydrophobicity of the filler (D0) surface is improved, and the adhesion between the filler (D0) and a matrix resin is improved, and thus it is possible to obtain the cardanol-modified filler (D) capable of improving strength and toughness.

The type of filler (D0) is not particularly limited, and examples thereof include particulate fillers such as silica, alumina, titanium oxide, iron oxide, zinc oxide, magnesium oxide, antimony oxide, barium ferrite, strontium ferrite, beryllium oxide, pumice stone, pumice balloon, aluminum hydroxide, magnesium hydroxide, calcium carbonate, magnesium carbonate, calcium sulfate, barium sulfate, ammonium sulfate, calcium sulfite, glass balloon, glass bead, carbon black, calcium silicate, potassium titanate, lead zirconate titanate, zinc borate, barium metaborate, calcium borate, and sodium borate; plate-like fillers such as talc, clay, mica, montmorillonite, bentonite, wollastonite, dolomite, dawsonite, and graphite; fibrous fillers such as glass fiber, carbon fiber, boron fiber, silicon carbide fiber, alumina fiber, aramid fiber, and metal fiber; and nano-fillers such as nano-silica, nano-clay, carbon nanotube, precious-metal nano particles, indium oxide nano particles, and calcium carbonate nano particles. Among these, from the viewpoint of improvements in strength, fibrous fillers and nano-fillers are preferred, and glass fiber or nano-silica, which has high reactivity with an alkoxy group possessed by the cardanol-modified silane coupling agent (C), is more preferred. These fillers (D0) can be used alone or in combination.

When the filler (D0) is subjected to a surface treatment with the cardanol-modified silane coupling agent (C), it is preferred that the cardanol-modified silane coupling agent (C) be diluted with a solvent and then the filler (D0) be immersed in the diluted solution or the diluted solution be sprayed onto the filler (D0) to adhere thereon, because of simple and easy handling. As the solvent, alcohols such as methanol and ethanol, and acetone, ethyl acetate, toluene, xylene, or the like can be used. The concentration of the cardanol-modified silane coupling agent (C) in the diluted solution can be set, for example, from 0.01% by weight to 20% by weight. Further, if about 2% by weight of an acetic acid solution is added to this diluted solution, hydrolysis of the cardanol-modified silane coupling agent (C) proceeds faster, and the diluted solution can be efficiently bonded to a surface of the filler (D0). Further, the cardanol-modified silane coupling agent (C) may be used alone; however, two or more types of the cardanol-modified silane coupling agent (C) may be used in combination, or may be used after being mixed with other anti-corrosive agents and coupling agents, and the like.

The proportion of the cardanol-modified silane coupling agent (C) contained in the cardanol-modified filler (D) is preferably 0.01% by weight to 10% by weight, and more preferably 0.1% by weight to 6.5% by weight, from the viewpoint of obtaining a sufficient effect of adhesion with a matrix resin. When the proportion of the cardanol-modified silane coupling agent (C) is excessively low, a sufficient effect of adhesion may not be obtained. When the proportion of the cardanol-modified silane coupling agent (C) is excessively high, a cardanol-modified silane coupling agent (C) that is not bonded to a surface of the filler exists high in volume, and therefore, the strength may lower.

3. Cellulose Resin Composition

A cellulose resin composition according to the exemplary embodiment contains the cardanol-modified filler (D) and the cellulose resin (E0), or contains the cardanol-modified silane coupling agent (C) and the filler (D0) and the cellulose resin (E0).

As for the cellulose resin (E0), cellulose or a derivative thereof (F) (hereinafter also referred to as "constituent (F)") can be used in its natural state.

Cellulose is a straight-chain polymer of β-glucose having a structure represented by the following Formula (F1), and each glucose unit has three hydroxyl groups.

[Chemical Formula 6]

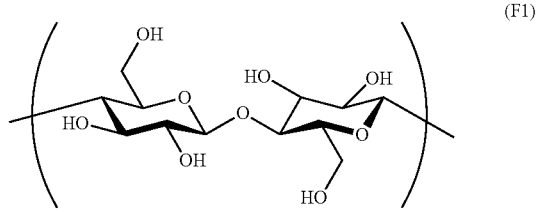

(F1)

Note that cellulose is a primary constituent of plants and trees and can be obtained by separating other constituents such as lignin from plants and trees. As cellulose, besides thus obtained ones, cotton and pulp highly containing cellulose may be used after being refined or may be used in their natural state.

Examples of the cellulose derivative include cellulose derivatives in which part of hydroxyl groups of cellulose is esterified, etherified or grafted. Specific examples thereof include organic acid esters such as cellulose acetate, cellulose butylate, and cellulose propionate; inorganic acid esters such as cellulose nitrate, cellulose sulfate, and cellulose phosphate; mixed esters such as cellulose acetate propionate, cellulose acetate butylate, cellulose acetate phthalate, and nitrate-acetate cellulose; and etherified celluloses such as methylcellulose, hydroxyethyl cellulose, and hydroxypropyl cellulose. In addition, examples thereof include cellulose to which styrene, (meth)acrylic acid, (meth)acrylic acid ester, ε-caprolactone, lactide, glycolide, or the like is grafted. These cellulose derivatives may be used alone or in combination.

Note that the term cellulose derivative encompasses any of cellulose compounds, and compounds having a cellulose skeleton, which are obtained by biologically or chemically introducing a functional group into cellulose used as a base material.

The polymerization degree of constituent (F) is, in terms of polymerization degree of glucose, preferably in the range of 50 to 5,000, and the range of 100 to 3,000 is more preferred. When the polymerization degree is excessively low, the strength and the heat resistance etc. of a produced resin may not be sufficient. In contrast, when the polymerization degree is excessively high, the melt viscosity of a produced resin becomes excessively high, which may cause a problem with molding of the produced resin.

In constituent (F), chitin and chitosan, which have similar structures to that of constituent (F), may be mixed. When chitin and chitosan are mixed therein, the total chitin/chitosan content to the total amount of the mixture is preferably 30% by mass or less, more preferably 20% by mass or less, and still more preferably 10% by mass or less.

As for the cellulose resin (E0), it is also possible to use a cellulose resin (E) in which cardanol or a derivative thereof (G) (hereinafter also referred to as "constituent (G)") is bonded, in a grafted state (hereinafter also referred to as "grafting"), to constituent (F), using the hydroxyl group. Note that as for constituent (G) to be grafted to constituent (F), it is possible to use those described above as constituent (A).

By using the thus grafted cellulose resin (E), mechanical properties (especially, toughness) and water resistance of the cellulose or the derivative thereof are improved, excellent thermo-plasticity is imparted, and further, adhesion to the cardanol-modified filler (D) can be improved. In addition, since both constituents (F) and (G) are inedible parts of plants, it is possible to increase the utilization factor of inedible parts.

The grafting can be performed by a dehydration bonding reaction between a cellulose hydroxyl group in constituent (F) and a phenolic hydroxyl group in constituent (G). At that time, a dehydration catalyst, such as sulfuric acid, toluene sulfonic acid, and hydrogen chloride, can be added. In this case, a cellulose carbon atom to which a cellulose hydroxyl group in constituent (F) is bonded is linked to a cardanol carbon atom to which a phenolic hydroxyl group in constituent (G) is bonded via an oxygen atom.

Further, the grafting can be performed by using a polyfunctional compound reactive with a cellulose hydroxyl group in constituent (F) and a phenolic hydroxyl group in constituent (G). In this case, a cellulose carbon atom to which a cellulose hydroxyl group in constituent (F) is bonded is linked to a cardanol carbon atom to which a phenolic hydroxyl group in constituent (G) is bonded via an organic linking group.

According to the grafting described above, grafting reaction efficiency can be improved and side reactions can be suppressed.

The organic linking group preferably contains a hydrocarbon group, and the number of carbon atoms of the hydrocarbon group is preferably one or more, more preferably 2 or more, whereas preferably 20 or less, more preferably 14 or less, and still more preferably 8 or less. If the number of carbon atoms is too large, the molecule is excessively large in size, causing a decrease in reactivity, and as the result, it may be difficult to increase the rate of grafting. As for such hydrocarbon group, a divalent hydrocarbon group is preferred. Examples thereof include divalent straight-chain aliphatic hydrocarbon groups (especially, straight-chain alkylene group) such as a methylene group, an ethylene group, a propylene group, a butylene group, a pentamethylene group, a hexamethylene group, a heptamethylene group, an octamethylene group, a decamethylene group, a dodecamethylene group, and a hexadecamethylene group; divalent alicyclic hydrocarbon groups such as a cycloheptane ring, a cyclohexane ring, a cyclooctane ring, a bicyclopentane ring, a tricyclohexane ring, a bicyclooctane ring, a bicyclononane ring, and a tricyclodecane ring; divalent aromatic hydrocarbon groups such as a benzene ring, a naphthalene ring, and a biphenylene group; and a divalent hydrocarbon group containing these hydrocarbon groups in combination.

As a functional group possessed by the polyfunctional compound, preferred is a functional group selected from a carboxyl group, a carboxylic acid anhydride group, a carboxylic acid halide group (especially, a carboxylic acid chloride group), an epoxy group, an isocyanate group, and a halogen group. Among these, a carboxyl group, a carboxylic acid anhydride group, and a halogen group (especially, a chloride group) are preferred. As a functional group to be reacted with a phenolic hydroxyl group in constituent (G), a carboxylic acid anhydride group, and a halogen group (especially, a chloride group) are particularly preferred. As a functional group to be reacted with a cellulose hydroxyl group in constituent (F), a carboxylic acid halide group (especially, a carboxylic acid chloride group) is particularly preferred, and which can be formed by subjecting a pre-grafted carboxyl group to acid-halogenation.

Specific examples of the polyfunctional compound include dicarboxylic acid, carboxylic acid anhydride, dicarboxylic acid halide, and monochlorocarboxylic acid. Examples of the dicarboxylic acid include malonic acid, succinic acid, glutaric acid, pimelic acid, suberic acid, azelaic acid, sebacic acid, dodecane dicarboxylic acid, and pentadecane dicarboxylic acid, hexadecane dicarboxylic acid. Examples of the carboxylic acid anhydride include anhydrides of these dicarboxylic acids. Examples of the dicarboxylic acid halide include acid halides of these dicarboxylic acid. Examples of the monochlorocarboxylic acid include rnonochloroacetic acid, 3-chloropropionic acid, 3-fluoropropionic acid, 4-chlorobutyric acid, 4-fluorobutyric acid, 5-chlorovaleric acid, 5-fluorovaleric acid, 6-chlorohexanoic acid, 6-fluorohexanoic acid, 8-chlorooctanoic acid, 8-fluorooctanoic acid, 12-chlorododecanoic acid, 12-fluorododecanoic acid, 18-chlorostearic acid, and 18-fluorostearic acid.

The cellulose resin (E) can be produced, for example, by using a functional group in the polyfunctional compound and a phenolic hydroxyl group in constituent (G) to bond the polyfunctional compound to constituent (G), and bonding, to constituent (F), a constituent obtained by using a functional group in the thus obtained constituent (a functional group derived from the polyfunctional compound) and a cellulose hydroxyl group in constituent (F).

For instance, when a carboxylic acid polyfunctional compound (dicarboxylic acid, carboxylic acid anhydride or monochlorocarboxylic acid) is used, after reacting a phenolic hydroxyl group in constituent (G) with a functional group in the polyfunctional compound (a carboxyl group, a carboxylic acid anhydride group or a halogen group (especially, a chloride group)), a remaining functional group (a carboxyl group) is converted into a carboxylic acid halide group (especially, a carboxylic acid chloride group). Then, by reacting this carboxylic acid halide group with a cellulose hydroxyl group in constituent (F), the cellulose resin (E) can be produced. In this case, the grafting can be extremely efficiently performed.

As a result of grafting using the polyfunctional compound, a cellulose carbon atom to which a cellulose hydroxyl group in constituent (F) is bonded and a hydrocarbon group in the polyfunctional compound are bonded, for example, via an ester bond, an ether bond or a urethane bond, preferably via an ester bond; and a cardanol carbon atom to which a phenolic hydroxyl group in constituent (G) is bonded and a hydrocarbon group in the polyfunctional compound are bonded, for example, via an ester bond, an ether bond or a urethane bond, preferably via an ester bond or an ether bond.

In the cellulose resin (E), it is preferred that an unsaturated bond(s) (double bond(s)) in straight-chain hydrocarbon parts of constituent (G) be hydrogenated and converted into a saturated bond(s). The conversion rate (hydrogenation rate) of the unsaturated bond through hydrogenation is preferably 90 mol % or higher, and more preferably 95 mol % or higher. A residual rate of the unsaturated bonds (the number of unsaturated bonds per molecule of cardanol) in constituent (G) that has undergone hydrogenation is preferably 0.2-bond/molecule or less, and more preferably 0.1-bond/molecule or less.

If constituent (G) is grafted to constituent (F), with many unsaturated bonds being contained in the straight-chain hydrocarbon parts of constituent (G), side reactions are prone to occur, grafting may not efficiently performed, and the solubility of the grafted product to the solvent may considerably lower. If constituent (G) having undergone hydrogenation, in which unsaturated bonds in the straight-chain hydrocarbon parts of constituent (G) have been sufficiently converted into saturated bonds, is grafted, side reactions are suppressed, grafting can be efficiently performed, and a decrease in solubility of the grafted product to a solvent can be suppressed.

The timing of hydrogenation of constituent (G) may be before reacting constituent (G) with the polyfunctional compound, before grafting constituent (G) to constituent (F) after reacting constituent (G) with the polyfunctional compound, or after grafting thereof to constituent (F). From the viewpoint of reaction efficiency etc. of hydrogenation and grafting, the timing of hydrogenation of constituent (G) is preferably before grafting thereof to constituent (F), and more preferably before reacting constituent (G) with the polyfunctional compound.

In the cellulose resin (E), the proportion (rate of grafting) of constituent (G) bonded to constituent (F) is expressed by the number of constituent (G) added (degree of substitution, hereinafter referred to as "$DS_{CD}$") per one glucose unit in constituent (F). $DS_{CD}$ is preferably 0.1 or higher, more preferably 0.2 or higher, and still more preferably 0.4 or higher. When $DS_{CD}$ is excessively low, an effect obtained from grafting may not be sufficient. The maximum value of $DS_{CD}$ is, theoretically, "3," however, from the viewpoint of ease of production (grafting), it is 2.5 or lower, more preferably 2 or lower, and still more preferably 1.5 or lower. Further, $DS_{CD}$ may be 1 or lower, and if so, a sufficiently improved effect can be obtained. When $DS_{CD}$ is high in number, there is a tendency that the maximum strength (tensile strength, bending strength) decreases, while the tensile rupture strain (toughness) increases, and thus it is preferable to suitably set $DS_{CD}$ in accordance with desired properties.

In the cellulose resin (E), along with grafting of constituent (G) to constituent (F), other reactive hydrocarbon compounds may be grafted to constituent (F). With this, it is possible to improve properties of the cellulose resin (E) to a desired level. Improvements of properties of the cellulose resin (E) are effected especially when the reactive hydrocarbon compound is placed so as to be embedded in spaces of a steric structure composed of constituent (G) which is grafted to constituent (F).

The reactive hydrocarbon compound may be a compound having at least one functional group reactive with a cellulose hydroxyl group in constituent (F). Examples thereof include a hydrocarbon compound having a carboxyl group. Specific examples thereof include monocarboxylic acids such as aliphatic monocarboxylic acid, aromatic carboxylic acid, and alicyclic monocarboxylic acid. Examples of the aliphatic monocarboxylic acid include a linear fatty acid or a branched fatty acid having a side chain.

The reactive hydrocarbon compound has a carbon number preferably in the range of 1 to 32, and more preferably in the range of 1 to 20. If the carbon number is too large, the molecule is excessively large in size, causing a decrease in reaction efficiency due to a steric hindrance, and as the result, it may be difficult to increase the rate of grafting. When the hydrocarbon group of the reactive hydrocarbon compound is an aromatic hydrocarbon group or an alicyclic hydrocarbon group, it is effective to improve especially rigidity and heat resistance, and when the hydrocarbon group of the reactive hydrocarbon compound is an aliphatic hydrocarbon group, it is effective to improve especially toughness.

Examples of the aliphatic carboxylic acid used as the reactive hydrocarbon compound include saturated fatty acids such as acetic acid, propionic acid, butyric acid, valeric acid, caproic acid, enanthic acid, caprylic acid, pelargonic acid, capric acid, 2-ethyl-hexane carboxylic acid, undecylenic acid, lauric acid, tridecylenic acid, mristic acid, pentadecylenic acid, palmitic acid, heptadecylenic acid, stearic acid, nonadecanoic acid, arachic acid, behenic acid, lignoceric acid, cerotic acid, heptacosanoic acid, montanic acid, melissic acid, lacceric acid, phenyl acetic acid, phenyl propionic acid, and cyclohexyl acetic acid; and unsaturated fatty acids such as butenoic acid, pentenoic acid, hexenoic acid, octenoic acid, undecylenic acid, oleic acid, sorbic acid, linoleic acid, linolenic acid, and arachidonic acid. These acids may further have a substituent.

Examples of the aromatic carboxylic acid used as the reactive hydrocarbon compound include benzoic acids; an aromatic carboxylic acid in which an alkyl group is introduced into a benzene ring of a benzoic acid, such as toluoylic acid; an aromatic carboxylic acid having two or more benzene rings, such as biphenyl carboxylic acid; an aromatic carboxylic acid having a condensed ring structure, such as naphthalene carboxylic acid, and tetralin carboxylic acid; and derivatives of these aromatic carboxylic acids.

Examples of the alicyclic monocarboxylic acid used as the reactive hydrocarbon compound include cyclopentane carboxylic acid, cyclohexane carboxylic acid, cyclooctane carboxylic acid, and derivatives thereof.

When an organic silicon compound or an organic fluorine compound is added into the structure of the reactive hydrocarbon compound, a further improved effect of water resistance and the like can be obtained.

Examples of a reactive functional group in the reactive hydrocarbon compound include, besides a carboxyl group; a carboxylic acid halide group (especially, a carboxylic acid chloride group), an epoxy group, an isocyanate group, and a halogen group (especially, a chloride group). Among these, a carboxyl group and a carboxylic acid halide group are preferred, and a carboxylic acid chloride group is particularly preferred. Examples of the carboxylic acid halide group (especially, carboxylic acid chloride group) include an acid halide group (especially, an acid chloride group), in which a carboxyl group of each of the above-mentioned various carboxylic acids is acid-halogenated.

The reactive hydrocarbon compound can be grafted in the step where constituent (G) is grafted to constituent (F). With this, the reactive hydrocarbon compound can be homogeneously grafted. These may be added all together, however, by adding the reactive hydrocarbon compound after grafting constituent (G) to constituent (F), the grafting reaction efficiency can be improved.

The grafting treatment can be carried out by heating, at an appropriate temperature, constituent (F), constituent (G), and when necessary the reactive hydrocarbon compound in a solvent capable of solving them. Cellulose is less prone to being dissolved in ordinary solvents, however, can be dissolved in a diemthylsulfoxide-amine solvent, a dimethylformamide-chloral-pyridine solvent, a dimethylacetoamide-lithium chloride solvent, an imidazolium ionic liquid, or the like. When the grafting reaction is performed in an ordinary solvent, a carboxylic acid or an alcohol is preliminarily bonded to part of cellulose hydroxyl groups in the cellulose to reduce the intermolecular force, and thereby it is possible to use a cellulose derivative with the solubility having been changed. Acylated cellulose in which hydrogen atoms of hydroxyl groups are substituted by an acyl group such as acetyl group, propionyl group, butyryl group or the like is preferred, and particularly preferred is cellulose acetate which is acetylated using an acetic acid or an acetyl chloride.

Among residual cellulose hydroxyl groups which have not been utilized for grafting, some cellulose hydroxyl groups remain as hydroxyl groups, and others are modified by acetylation or the like, as described above. There is a tendency that the larger the quantity of hydroxyl groups is, the higher the maximum strength and the heat resistance become, whereas there is a tendency that the larger the water absorbing property is. There is a tendency that the higher the modification rate of cellulose hydroxyl groups through acetylation or the like is, the lower the water absorbing property is and the greater the plasticity and rupture strain become, while there is a tendency that the greater the maximum strength and heat resistance become. In view of these tendencies and grafting conditions, the conversion rate of hydroxyl groups can be suitably set.

From the viewpoints of water absorbing property, mechanical strength, heat resistance and further, the grafting treatment, it is preferred that the cellulose hydroxyl groups be appropriately acylated (especially, acetylated). From the viewpoint of obtaining a sufficient acylation effect, the number of acyl groups added (degree of substitution, $DS_{ACE}$) per one glucose unit in constituent (F) is preferably 0.5 or more, more preferably 1.0 or more, and still more preferably 1.5 or more. Furthermore, from the viewpoint of sufficiently securing the rate of grafting ($DS_{CD}$), the degree of substitution $DS_{ACE}$ of acyl groups is preferably 2.5 or lower, and still more preferably 2.2 or lower.

When producing a cellulose resin composition, the cardanol-modified filler (D) can be mixed in the cellulose resin (E0). Further, after the filler (D0) and the cardanol-modified silane coupling agent (C) are mixed in the cellulose resin (E0), it is also possible to bond the cardanol-modified silane coupling agent (C) to a surface of the filler (D0) through reactive processing. The mixing method is not particularly limited, and mixing by a known mixer, for example, a tumbler, a ribbon blender, a uniaxial or biaxial kneader, and melt-mixing by an extruder, a roll or the like can be utilized.

The amount of the filler (cardanol-modified filler (D) or filler (D0)) contained in the cellulose resin composition is preferably 3 parts by weight to 100 parts by weight with respect to 100 parts by weight of the cellulose resin (E0). When the mixing amount of the filler is 3 parts by weight or more, a reinforcing effect by the filler can be sufficiently developed, and when the amount is 100 parts by weight or less, the flowability does not so decrease, and a reduction in moldability can be suppressed.

The mixing amount of the cardanol-modified silane coupling agent (C) to the mixing amount of filler (D0) is preferably 0.01% by weight to 10% by weight, and more preferably 0.1% by weight to 6.5% by weight. When the mixing amount of the cardanol-modified silane coupling agent (C) is excessively low, a sufficient adhesion effect may not be obtained. Further, when the mixing amount of the cardanol-modified silane coupling agent (C) is excessively high, the amount of the cardanol-modified silane coupling agent (C) that is not directly bonded to a surface of the filler (D0) increases, and the strength may lower.

The thus obtained cellulose resin composition not only allows for improvements in adhesion between a resin and a filler and in the strength, but also has excellent toughness, which is improved by an interaction of flexible straight-chain hydrocarbon parts of cardanol. In addition, since both the cellulose resin (E0) and cardanol are inedible parts of plants, it is possible to increase the utilization factor of inedible parts in the resin composition.

In the cellulose resin composition, various additives used for ordinary thermoplastic resins can be used. For instance, by adding a plasticizer to the cellulose resin composition, flowability and elongation at the time of fracture can be further improved. Examples of such plasticizers include phthalates such as dibutyl phthalate, diallyl phthalate, diethyl phthalate, dimethyl phthalate, di-2-methoxyethyl phthalate, ethylphthalyl-ethyl glycolate, and methylphthalyl-ethyl glycolate; tartrates such as dibutyl tartrate; adipates such as dioctyl adipate, and di-isononyl adipate; polyhydric alcohol esters such as triacetin, diacetyl glycerin, tripropionitrile glycerin, and glycerin monostearate; phosphates such as triethyl phosphate, triphenyl phosphate, and tricresyl phosphate; dibasic fatty acid esters such as dibutyl adipate, dioctyl adipate, dibutyl azelate, dioctyl azelate, and dioctyl sebacate; citrates such as triethyl citrate, acetyl-triethyl citrate, and tributyl acetyl citrate; epoxidized vegetable oils such as epoxidized soybean oil, and epoxidized linseed oil; benzoates such as ethyl-O-benzoylbenzoat, aliphatic dicarboxylic acid esters such as sebacate, and azelate; unsaturated dicarboxylic acid esters such as maleate; and others such as N-ethyl toluenesulfonamide, triacetin, O-cresyl p-toluenesulfonate, and tripropionin.

Besides, to the cellulose resin composition, typical thermoplastic resins may be added if needed. In addition, to the cellulose resin composition, additives for use in typical resin compositions, such as fire retardant, colorant, antioxidant, and thermal stabilizer, may be added if needed.

EXAMPLES

Hereinafter, the exemplary embodiment will be further described in detail using concrete Examples.

Synthesis Example 1

Production of Cardanol Derivative for Grafted Cellulose Resin (Chloride of Monochloroacetic Acid-Modified Cardanol)

Using, as a base material, a hydrogenated cardanol (produced by ACROS Organics, m-n-pentadecylphenol), in which unsaturated bonds of straight-chain hydrocarbon moiety of cardanol were hydrogenated, a phenolic hydroxyl group thereof was reacted with a monochloroacetic acid to provide the hydrogenated cardanol with a carboxyl group, thereby obtaining a carboxylated hydrogenated cardanol. Next, the carboxyl group in the carboxylated hydrogenated cardanol was chloridized with an oxalyl chloride to be converted into an acid chloride group, thereby obtaining a chloridized hydrogenated cardanol.

Specifically, the chloridized hydrogenated cardanol was obtained according to the following procedures.

First, 80 g (0.26 mol) of a hydrogenated cardanol was dissolved in 120 mL of methanol, and an aqueous solution obtained by dissolving 64 g (1.6 mol) of sodium hydroxide in 40 mL of distilled water was added thereto. Thereafter, a solution obtained by dissolving 66 g (0.70 mol) of a monochloroacetic acid produced by Kanto Chemical Co., Inc. in 50 mL of methanol was dropped into the hydrogenated cardanol solution at the room temperature. Upon completion of the dropping, the solution was continuously stirred under reflux at 73° C. for 4 hours. After the reaction solution was cooled to room temperature, the reaction mixture was acidified with a diluted hydrochloric acid until the pH thereof was 1 (pH=1), and then 250 mL of methanol, 500 mL of diethylether, further, 200 mL of distilled water were added to the reaction mixture. An aqueous layer was separated and disposed by a separating funnel, and an ether layer was washed with 400 mL of distilled water twice. The ether layer was dried on magnesium anhydride and then the magnesium anhydride was filtered off. The obtained filtrate (ether layer) was concentrated under a reduced pressure (90° C./3 mmHg) by an evaporator to obtain a yellow-brown powdery crude product as a residue. This crude product was recrystallized from n-hexane and dried in vacuum, thereby obtaining 46 g (0.12 mol) of an intended white powder of carboxylated hydrogenated cardanol.

46 g (0.12 mol) of the obtained carboxylated hydrogenated cardanol was dissolved in 250 mL of dehydrated chloroform, 24 g (0.19 mol) of oxalyl chloride and 0.25 mL (3.2 mmol) of N,N-dimethylformamide were added thereto, and the mixture was stirred at room temperature for 72 hours. The chloroform and a surplus oxalyl chloride were distilled away under reduced pressure, thereby obtaining 48 g (0.13 mol) of chloridized hydrogenated cardanol.

Synthesis Example 2

Production of Cellulose Resin 1 (Cardanol-Grafted Cellulose Acetate)

The chloridized hydrogenated cardanol (cardanol derivative) produced in Synthesis Example 1 was subjected to grafting to a cellulose acetate (produced by Daicel Chemical Industries, Ltd., product name: LM-80, the additional number of acetic acid per glucose unit in cellulose (degree of substitution of acetyl group: $DS_{ACE}$=2.1), thereby obtaining a grafted cellulose acetate.

Specifically, the grafted cellulose acetate was obtained according to the following procedures.

10 g of cellulose acetate (quantity of hydroxyl group: 0.036 mol) was dissolved in 200 mL of dehydrated dioxane, and 5.0 mL (0.036 mol) of triethylamine was added as a reaction catalyst and an acid scavenger. To this solution, 100 mL of a dioxane solution, in which 46 g (0.11 mol) of the chloridized hydrogenated cardanol produced in Synthesis Example 1 had been dissolved, was added, and then heated at 100° C. for 6 hours under reflux. The reaction solution was slowly dropped into 3 L of methanol while stirring so as to be reprecipitated, and a solid was filtered out. The filtered solid was air-dried overnight and further dried in vacuum at 105° C. for 5 hours, thereby obtaining 20 g of a grafted cellulose acetate.

The obtained sample (grafted cellulose acetate) was measured by $^1$H-NMR (manufactured by Bruker, product name: AV-400, 400 MHz) and found to have a $DS_{CD}$ of 0.80.

Synthesis Example 3

Production of Cellulose Resin 2 (Cardanol-Grafted Cellulose Acetate)

The chloridized hydrogenated cardanol (cardanol derivative) produced in Synthesis Example 1 was subjected to grafting to a cellulose acetate (produced by Daicel Chemical Industries, Ltd., product name: LM-80, the additional number of acetic acid per glucose unit in cellulose (degree of substitution of acetyl group: $DS_{ACE}$=2.1), thereby obtaining a grafted cellulose acetate.

Specifically, the grafted cellulose acetate was obtained according to the following procedures.

10 g of cellulose acetate (quantity of hydroxyl group: 0.036 mol) was dissolved in 200 mL of dehydrated dioxane, and 5.0 mL (0.036 mol) of triethylamine was added as a reaction catalyst and an acid scavenger. To this solution, 100 mL of a dioxane solution, in which 14 g (0.037 mol) of the chloridized hydrogenated cardanol produced in Synthesis Example 1 had been dissolved, was added, and then heated at 100° C. for 3 hours under reflux. The reaction solution was slowly dropped into 3 L of methanol while stirring so as to be reprecipitated, and a solid was filtered out. The filtered solid was air-dried overnight and further dried in vacuum at 105° C. for 5 hours, thereby obtaining 15 g of grafted cellulose acetate.

The obtained sample (grafted cellulose acetate) was measured by $^1$H-NMR (manufactured by Bruker, product name: AV-400, 400 MHz) and found to have a $DS_{CD}$ of 0.55.

Example 1

Production of Cardanol-Modified Silane Coupling Agent 1

A hydrogenated cardanol (produced by ACROS Organics, m-n-pentadecylphenol), in which unsaturated bonds of straight-chain hydrocarbon moiety of cardanol were hydrogenated, was bonded to γ-isocyanatopropyl triethoxy silane (produced by Shin-Etsu Chemical Co., Ltd., product name: KBE-9007) to obtain cardanol-modified silane coupling agent 1.

Specifically, cardanol-modified silane coupling agent 1 was obtained according to the following procedures.

Into a nitrogen-purged reaction vessel, 3.42 g (11.2 mmol) of the hydrogenated cardanol was charged, heated to 80° C. so as to be molten, and 0.05 mol % dibutyl tin dilaurate was added as a catalyst. To this liquid, 3.00 g (12.1 mmol) of γ-isocyanatopropyl triethoxy silane was added, and stirred at 80° C. for 30 minutes. The obtained product was cooled to room temperature, thereby obtaining 6.2 g of a reaction product.

The obtained sample (cardanol-modified silane coupling agent 1) was measured by $^1$H-NMR (manufactured by Bruker, product name: AV-400, 400 MHz), and found that the amount of the 1:1 reaction product of hydrogenated cardanol and γ-isocyanatopropyl triethoxy silane was 90% by weight or more.

Example 2

Production of Cardanol-Modified Silane Coupling Agent 2

A hydrogenated cardanol (produced by ACROS Organics, m-n-pentadecylphenol), in which unsaturated bonds of straight-chain hydrocarbon moiety of cardanol were hydrogenated, was bonded to γ-glycidyloxypropyl triethoxy silane (produced by Shin-Etsu Chemical Co., Ltd., product name: KBE-403) to obtain cardanol-modified silane coupling agent 2.

Specifically, cardanol-modified silane coupling agent 2 was obtained according to the following procedures.

Into a nitrogen-purged reaction vessel, 3.42 g (11.2 mmol) of the hydrogenated cardanol was charged, heated to 80° C. so as to be molten, and 0.5 mol % triphenylphosphine was added as a catalyst. To this liquid, 3.36 g (12.1 mmol) of γ-glycidyloxypropyl triethoxy silane was added, and stirred at 80° C. for 1 hour. The obtained product was cooled to room temperature, thereby obtaining 6.5 g of a reaction product.

The obtained sample (cardanol-modified silane coupling agent 2) was measured by $^1$H-NMR (manufactured by Bruker, product name: AV-400, 400 MHz), and found that the amount of the 1:1 reaction product of hydrogenated cardanol and γ-glycidyloxypropyl triethoxy silane was 90% by weight or more.

Example 3

Production of Cardanol-Modified Glass Fiber 1

Using cardanol-modified silane coupling agent 1 produced in Example 1, a glass fiber (produced by Owence Corning, product name: CS03JAFT592, fiber diameter: 10 μm, 3 mm chopped strand, heating shrinkage: 1.0%) was subjected to a surface treatment, thereby obtaining cardanol-modified glass fiber 1.

Specifically, cardanol-modified glass fiber 1 was obtained according to the following procedures.

1.0 g of cardanol-modified silane coupling agent 1 was dissolved in 50 ml of ethanol and 10 g of glass fiber were immersed thereto. After this solution was stirred overnight, the solution was sequentially dried in vacuum at 80° C. for 2 hours, at 120° C. for 2 hours to remove the solvent, 50 ml of ethanol was added again to wash a residue, and the residue was filtered out. After this washing operation was repeated four times, the reaction product was dried in vacuum at 105° C. for 3 hours, thereby obtaining cardanol-modified glass fiber 1.

A heating shrinkage of the obtained sample (cardanol-modified glass fiber 1) was measured at 800° C. by TGA (manufactured by Seiko Instruments, Inc., product name: TGA6000) and found to be 2.9% by weight, and thus the proportion (coupling agent content) of cardanol-modified silane coupling agent 1 contained in cardanol-modified glass fiber 1 was calculated as 1.9% by weight.

Example 4

Production of Cardanol-Modified Glass Fiber 2

Using cardanol-modified silane coupling agent 1 produced in Example 1, a glass fiber (produced by Owence Corning, product name: CS03JAFT592, fiber diameter: 10 μm, 3 mm chopped strand, heating shrinkage: 1.0%) was subjected to a surface treatment, thereby obtaining cardanol-modified glass fiber 2.

Specifically, cardanol-modified glass fiber 2 was obtained according to the following procedures.

1.0 g of cardanol-modified silane coupling agent 1 was dissolved in 50 ml of ethanol, 10 ml of 2% by weight acetic acid aqueous solution was added and 10 g of glass fiber was immersed to this mixed solution. After this solution was stirred overnight, the solution was sequentially dried in vacuum at 80° C. for 2 hours, at 120° C. for 2 hours to remove the solvent, 50 ml of ethanol was added again to wash a residue, and the residue was filtered out. After this washing operation was repeated four times, the reaction product was dried in vacuum at 105° C. for 3 hours, thereby obtaining cardanol-modified glass fiber 2.

A heating shrinkage of the obtained sample (cardanol-modified glass fiber 2) was measured at 800° C. by TGA (manufactured by Seiko Instruments, Inc., product name: TGA6000) and found to be 7.2% by weight, and thus the proportion of cardanol-modified silane coupling agent 1 contained in cardanol-modified glass fiber 1 was calculated as 6.2% by weight.

Example 5

A mixture containing 100 parts by weight of cellulose resin 1 produced in Synthesis Example 2 and 25 parts by weight of cardanol-modified glass fiber 1 produced in Example 3 were blended by an extruder (HAAKE MiniLab Rheomex extruder (Model CTW5, Thermo Electron Corp., Waltham, Mass.)) (temperature: 200° C., screw revolving speed: 50 rpm), thereby producing a cellulose resin composition.

This resin composition was press-molded to obtain a molded product.

(Molding Conditions)

Temperature: 200° C., time: 2 minutes, pressure: 100 kgf ($9.8 \times 10^2$ N), Size of molded product: thickness: 2 mm, width: 13 mm, length: 80 mm The molded product obtained by the above molding was subjected to a bending test according to JIS K 7171. The results are shown in Table 1.

Examples 6 and 7, Comparative Examples 1, 3 and 4

Cellulose resin compositions and molded products were produced in substantially the same manner as in Example 1, except that the composition shown in Tables 1 and 2 was employed, and a bending test was performed in the same manner as in Example 5. The results are shown in Table 1.

Comparative Examples 2 and 5

Cellulose resins 1 and 2 respectively produced in Synthesis Examples 2 and 3 were press-molded under the molding conditions described in Example 5 to produce molded products, and a bending test was performed in the same manner as in Example 5. The results are shown in Tables 1 and 2.

TABLE 1

|  | Example 5 | Comparative Example 1 | Comparative Example 2 |
| --- | --- | --- | --- |
| Cellulose resin 1 [parts by weight] ($DS_{CD}$: 0.80) | 100 | 100 | 100 |
| Cardanol-modified glass fiber 1 [parts by weight] (Coupling agent content: 1.9% by weight) | 25 |  |  |
| Conventional glass fiber A* |  | 25 |  |
| Bending strength [MPa]** | 45 (increased by 22%) | 40 (increased by 8%) | 37 |
| Elastic modulus in bending [GPa] | 1.7 | 1.6 | 0.9 |
| Bending rupture strain [%] | 6 | 4 | >10 |

*Produced by Owence Corning, product name: CS03JAFT592, fiber diameter: 10 μm, 3 mm chopped strand, heating shrinkage: 1.0% (glass fiber used as a base material of Cardanol-modified glass fiber 1)
**Numerals in parentheses are strength increase rates relative to the strength of Comparative Example 2 (only Cellulose resin 1)

TABLE 2

|  | Example 6 | Example 7 | Comparative Example 3 | Comparative Example 4 | Comparative Example 5 |
| --- | --- | --- | --- | --- | --- |
| Cellulose resin 2 [parts by weight] ($DS_{CD}$: 0.55) | 100 | 100 | 100 | 100 | 100 |
| Cardanol-modified glass fiber 1 [parts by weight] (Coupling agent content: 1.9% by weight) | 25 |  |  |  |  |
| Cardanol-modified glass fiber 2 [parts by weight] (Coupling agent content: 6.2% by weight) |  | 25 |  |  |  |
| Conventional glass fiber A* |  |  |  | 25 |  |
| Conventional glass fiber B** |  |  |  |  | 25 |

TABLE 2-continued

|  | Example 6 | Example 7 | Comparative Example 3 | Comparative Example 4 | Comparative Example 5 |
|---|---|---|---|---|---|
| Bending strength [MPa]*** | 66 (increased by 29%) | 63 (increased by 24%) | 59 (increased by 16%) | 57 (increased by 12%) | 51 |
| Elastic modulus in bending [GPa] | 2.2 | 2.2 | 2.2 | 2.1 | 1.2 |
| Bending rupture strain [%] | 8 | >10 | 6 | >10 | >10 |

*Produced by Owence Corning, product name: CS03JAFT592, fiber diameter: 10 μm, 3 mm chopped strand, heating shrinkage: 1.0% (glass fiber used as a base material of Cardanol-modified glass fiber 1)
**Produced by Owence Corning, product name: CS03JAFT692, fiber diameter: 10 μm, 3 mm chopped strand, heating shrinkage: 1.0%
***Numerals in parentheses are strength increase rates relative to the strength of Comparative Example 5 (only Cellulose resin 2)

When comparing the molded product of Example 5 to which a cardanol-modified glass fiber was added, with the molded product of Comparative Example 1 to which a conventional glass fiber was added, both molded products had an improved bending strength and less bending rupture strain, in comparison with the molded product of Comparative Example 2 to which no glass fiber was added. However, the bending strength increase rate of the molded product of Example 5 was about 2.7 times that of the molded product of Comparative Example 1, and the bending rupture strain of the molded product of Example 5 was 1.5 times that of the molded product of Comparative Example 1.

Further, when comparing the molded products of Examples 6 and 7 to which a cardanol-modified glass fiber was added, with the molded product of Comparative Example 3 to which a conventional glass fiber was added, any of these molded products had an improved bending strength, in comparison with the molded product of Comparative Example 5 to which no glass fiber was added. However, both the molded products of Examples 6 and 7 had a great bending strength improving effect, i.e., a bending strength increase rate of 20% or higher. In addition, the molded product of Comparative Example 4, to which another conventional glass fiber was added, had much less bending strength improving effect than that of the molded product of Comparative Example 3, although it was excellent in bending rupture strain.

The invention claimed is:

1. A cardanol-modified silane coupling agent (C) obtained by reacting cardanol or a derivative thereof (A) with an epoxy silane coupling agent or an isocyanate silane coupling agent (B).

2. A cardanol-modified filler (D), in which a filler (D0) is subjected to a surface treatment with the cardanol-modified silane coupling agent (C) according to claim 1.

3. The cardanol-modified filler (D) according to claim 2, wherein the filler (D0) is a glass fiber.

4. A cellulose resin composition comprising:
the cardanol-modified filler (D) according to claim 3 and
a cellulose resin (E0).

5. A cellulose resin composition comprising:
the cardanol-modified filler (D) according to claim 2, and
a cellulose resin (E0).

6. The cellulose resin composition according to claim 5, wherein the cellulose resin (E0) is a cellulose resin (E) in which cellulose or a derivative thereof (F) is bonded to cardanol or a derivative thereof (G) using a cellulose hydroxyl group in the cellulose or the derivative thereof (F) and a phenolic hydroxyl group in the cardanol or the derivative thereof (G).

7. The cellulose resin composition according to claim 6, wherein in the cellulose resin (E), a cellulose carbon atom to which the cellulose hydroxyl group in the cellulose or the derivative thereof (F) is bonded is linked to a cardanol carbon atom to which the phenolic hydroxyl group in the cardanol or the derivative thereof (G) is bonded via an organic linking group containing a divalent hydrocarbon group.

8. The cellulose resin composition according to claim 7, wherein in the cellulose resin (E), the cellulose carbon atom is bonded to the divalent hydrocarbon group via any one of an ester bond, an ether bond and a urethane bond; and the cardanol hydrocarbon atom is bonded to the divalent hydrocarbon group via any one of an ester bond, an ether bond and a urethane bond.

9. The cellulose resin composition according to claim 8, wherein in the cellulose resin (E), a degree of substitution of the cardanol or the derivative thereof (G) per a glucose unit in the cellulose or the derivative thereof (F) is 0.1 or higher.

10. The cellulose resin composition according to claim 7, wherein in the cellulose resin (E), a degree of substitution of the cardanol or the derivative thereof (G) per a glucose unit in the cellulose or the derivative thereof (F) is 0.1 or higher.

11. The cellulose resin composition according to 7, wherein in the cellulose resin (E), an unsaturated bond in the cardanol or the derivative thereof (G) is converted into a saturated bond.

12. The cellulose resin composition according to claim 6, wherein in the cellulose resin (E), a degree of substitution of the cardanol or the derivative thereof (G) per a glucose unit in the cellulose or the derivative thereof (F) is 0.1 or higher.

13. The cellulose resin composition according to claim 6, wherein in the cellulose resin (E), an unsaturated bond in the cardanol or the derivative thereof (G) is converted into a saturated bond.

14. A cellulose resin composition comprising:
the cardanol-modified silane coupling agent (C) according to claim 1,
a filler (D0), and
a cellulose resin (E0).

15. The cellulose resin composition according to claim 14, wherein the cellulose resin (E0) is a cellulose resin (E) in which cellulose or a derivative thereof (F) is bonded to cardanol or a derivative thereof (G) using a cellulose hydroxyl group in the cellulose or the derivative thereof (F) and a phenolic hydroxyl group in the cardanol or the derivative thereof (G).

16. The cellulose resin composition according to claim 15, wherein in the cellulose resin (E), a cellulose carbon atom to which the cellulose hydroxyl group in the cellulose or the derivative thereof (F) is bonded is linked to a cardanol carbon atom to which the phenolic hydroxyl group in the cardanol or the derivative thereof (G) is bonded via an organic linking group containing a divalent hydrocarbon group.

17. The cellulose resin composition according to claim 16, wherein in the cellulose resin (E), the cellulose carbon atom is bonded to the divalent hydrocarbon group via any one of an ester bond, an ether bond and a urethane bond; and the cardanol hydrocarbon atom is bonded to the divalent hydrocarbon group via any one of an ester bond, an ether bond and a urethane bond.

18. The cellulose resin composition according to claim 15, wherein in the cellulose resin (E), a degree of substitution of the cardanol or the derivative thereof (G) per a glucose unit in the cellulose or the derivative thereof (F) is 0.1 or higher.

19. The cellulose resin composition according to claim 15, wherein in the cellulose resin (E), an unsaturated bond in the cardanol or the derivative thereof (G) is converted into a saturated bond.

20. The cardanol-modified filler (D) according to claim 4, wherein the filler (D0) is a glass fiber.

* * * * *